United States Patent [19]
Brown et al.

[11] Patent Number: 5,118,193
[45] Date of Patent: Jun. 2, 1992

[54] APPARATUS AND METHOD FOR INSPECTION

[75] Inventors: Mark D. Brown, Carrollton; Stephen B. Kaiser, Flower Mound, both of Tex.

[73] Assignee: Texas Instruments Incorporated, Dallas, Tex.

[21] Appl. No.: 495,826

[22] Filed: Mar. 19, 1990

[51] Int. Cl.⁵ .................... G01B 11/00; F21V 30/00
[52] U.S. Cl. .................................... 356/394; 356/237
[58] Field of Search .................. 356/394, 237; 382/8

[56] References Cited

U.S. PATENT DOCUMENTS

| | | | |
|---|---|---|---|
| 4,578,810 | 3/1986 | MacFarlane et al. | 356/394 |
| 4,677,473 | 6/1987 | Okamoto et al. | 356/376 |
| 4,695,157 | 9/1987 | Schoenbaum et al. | 356/446 |

Primary Examiner—Richard A. Rosenberger
Attorney, Agent, or Firm—B. Peter Barndt; Richard L. Donaldson; William E. Hiller

[57] ABSTRACT

An apparatus and method for inspecting coatings on the surface of an object includes a light source of a ring light to uniformly light an object that is placed inside a diffusing view chamber. A video system measures the reflected light intensity from the surface of the object to determine if there are voids in the surface coating.

7 Claims, 4 Drawing Sheets

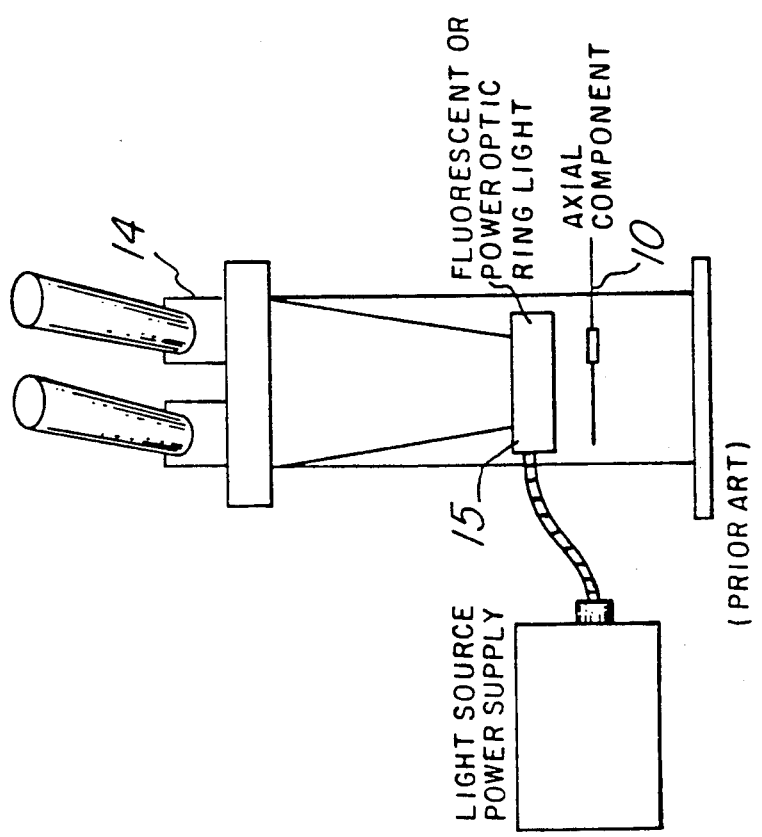
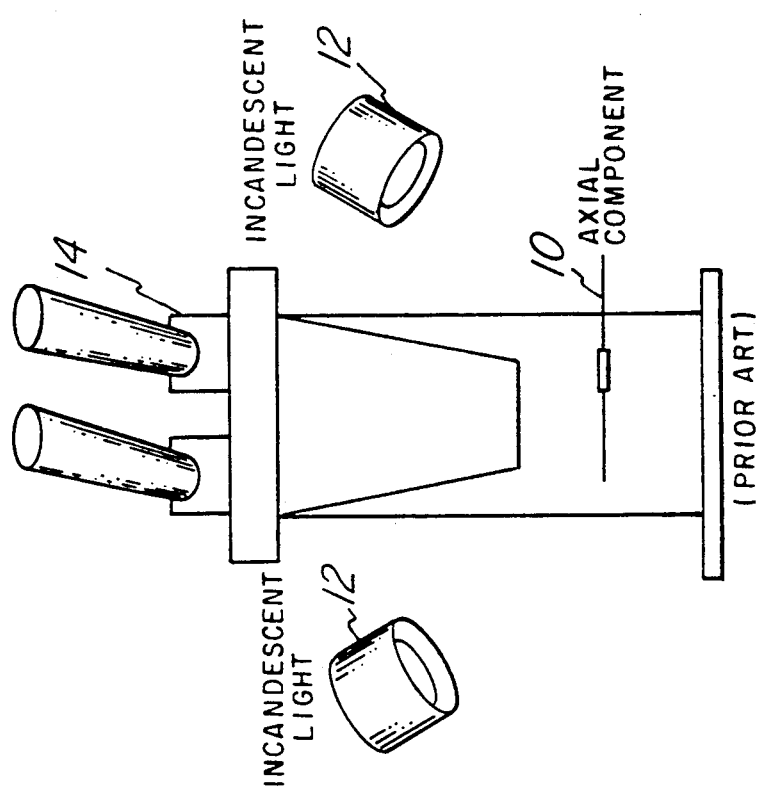

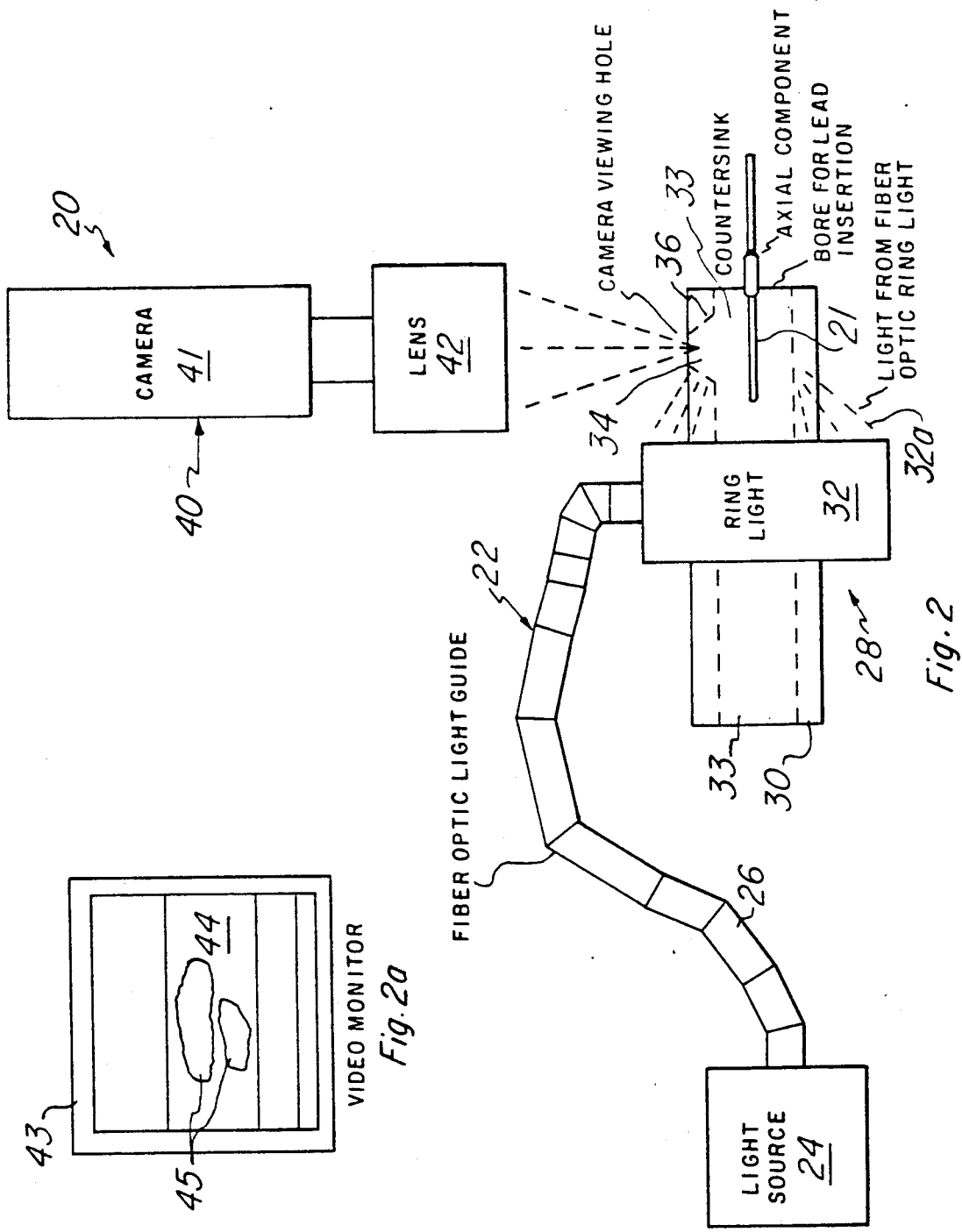

CROSS SECTION A-A

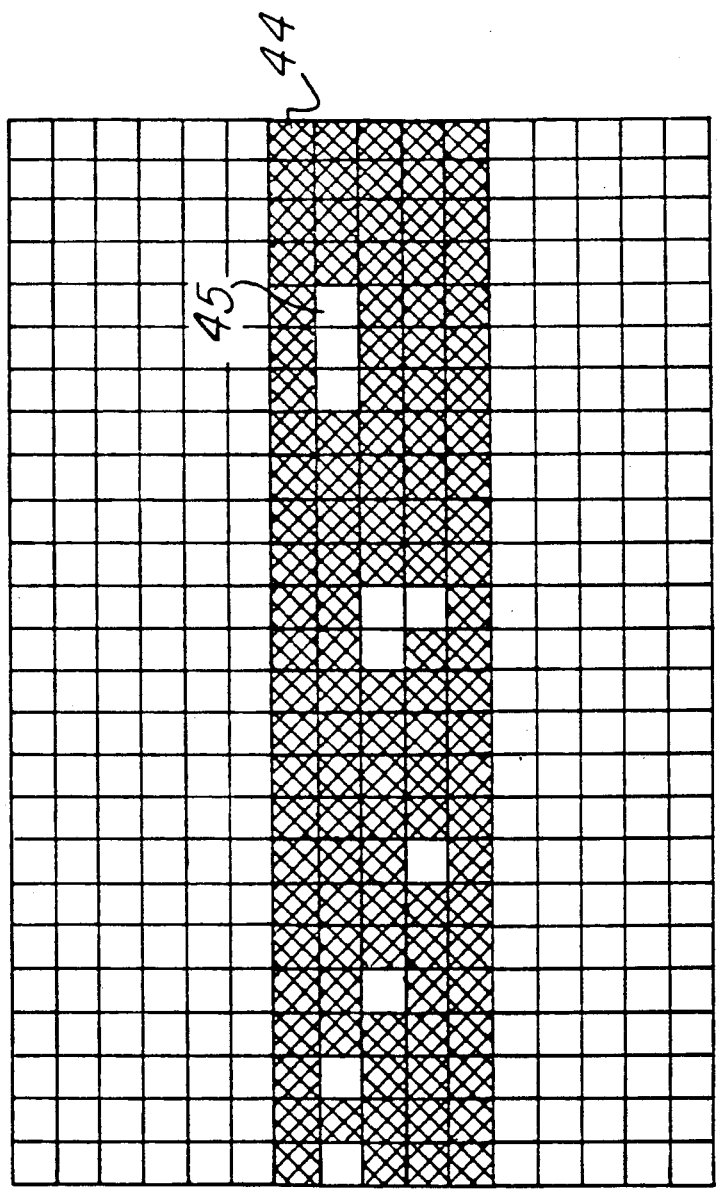

APPARATUS AND METHOD FOR INSPECTION

FIELD OF THE INVENTION

This invention relates to inspection systems and specifically to automatic part inspection systems.

BACKGROUND OF THE INVENTION

It is frequently necessary to visually inspect electronic parts for defects and quality. In particular, many types of electrical components used in various military projects must undergo various types of inspection and/or test. One inspection which components must undergo is that required by Military Specification 202F. That specification requires that leads be pretinned and inspected. Quality control guidelines dictate that thirteen leads out of each component lot be inspected for 95% solder coverage.

The prior art inspection systems are in large part manual and highly labor intensive. Human operators visually inspect the leads with a 10× microscope. The operator positions the lead under the microscope, and estimates the amount of solder coverage. The estimate requires the operator to determine the area of the lead covered by defects. This visual method has serious drawbacks caused by operator eye fatigue and difficulty in estimating the area of the lead covered by defects. Furthermore, the method averages between 10 and 30 seconds depending on the lead size.

The prior art inspection methods utilized incandescent or flourescent lights positioned above the components and around the eyepiece of the microscope, or fiber optic light rings positioned around the objective lens of the microscope above the lead. All of these lighting techniques produced lead images with numerous reflective glare spots and dark spots, regardless of the actual solder coating on the leads. The appearance of the uncoated or defective areas of the lead changed depending upon how the lead was positioned relative to the light source and the lens.

The change in appearance contributed to the problems with visual inspection systems, particularly with respect to consistency of results.

SUMMARY OF THE INVENTION

It is a purpose of the invention to provide an apparatus and method for automating solderability inspection to improve inspection consistency, eliminate operator judgment and eliminate a tedious inspection task. It is a further object of the invention to provide an apparatus for providing a detailed, glare free image of component leads. It is a further object of the invention to provide a vision system for the automated solderability inspection of component leads.

BRIEF DESCRIPTION OF THE DRAWINGS

FIG. 1 is a pictorial depiction of a prior art method of solderability inspection.

FIG. 1a is a pictorial depiction of another prior art method of solderability inspection.

FIG. 2 is a diagrammatic depiction of the preferred embodiment of the present invention.

FIG. 4 is a pictorial depiction of the pixel overlay of the image field with lead of the present invention.

DETAILED DESCRIPTION OF THE PREFERRED EMBODIMENT

Figure 3B:
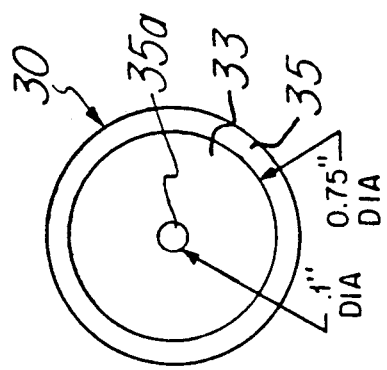
FIG. 3b is an end view of the light diffuser of FIG. 3.

Prior art methods of solderability inspection are shown in FIG. 1 and FIG. 1a. As shown in FIG. 1, a component 10 to be inspected is illuminated by incandescent lights 12 under a 10× microscope 14, and the lead is visually inspected by an operator. FIG. 1a shows a prior art system with a flourescent or fiber optic ring light 15 for illumination of component 10.

The preferred embodiment of the present invention is illustrated in FIG. 2, in which the inspection system of the present invention is generally referred to with the reference numeral 20. The inspection system 20 includes a lighting apparatus 22. The lighting apparatus 22 has a light source 24, and a light transmission device 26. The light transmission device 26 is preferably a fiber optic light guide.

The light transmission device 26 terminates in a light diffusing assembly 28. The light diffusing assembly 28 includes a light diffuser 30 and a fiber optic ring light 32. The light diffuser is preferably cylindrical in shape and made of a white translucent plastic material, such as nylon.

As shown in FIG. 2, the light diffuser 30 has a hollow inner viewing chamber 33, adapted to receive the component being inspected. The viewing chamber 33 is coaxial with the body of the diffuser 30. A hole 34 is formed through the body of diffuser 30 into viewing chamber 33. The hole 34 provides a port for viewing the component being inspected. As can be seen from FIG. 2, the hole 34 may have sloping sidewalls 36, which lessen shadowing caused by the hole 34. In place of the viewing hole 34, a viewing slot may also be utilized, which provides a larger viewing area.

Figure 3C:
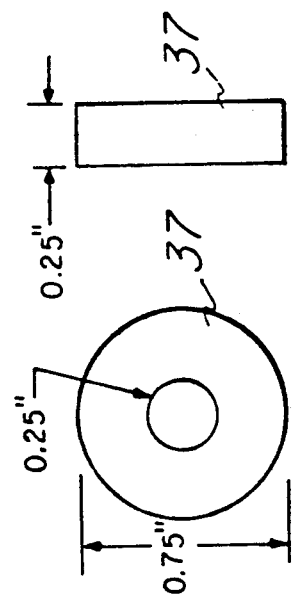
FIG. 3c is a view of a portion of the light diffuser of FIG. 3.
Figure 3:
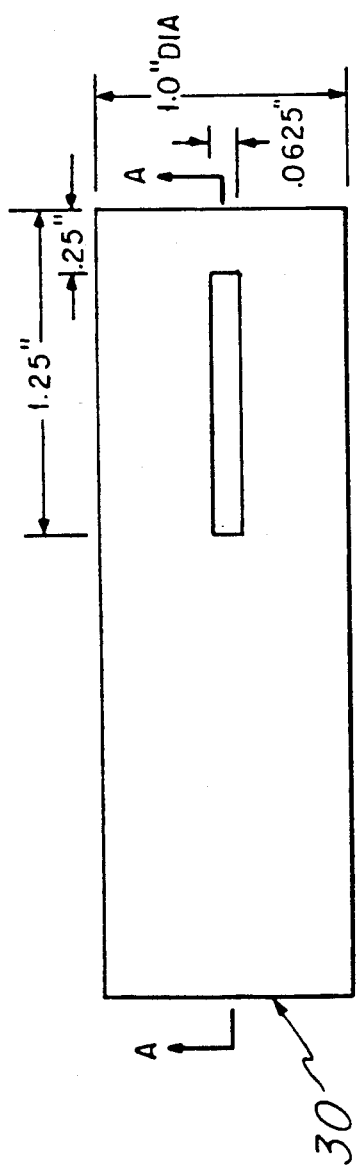
FIG. 3 is a plan view of a light diffuser used with the present invention.
Figure 3A:
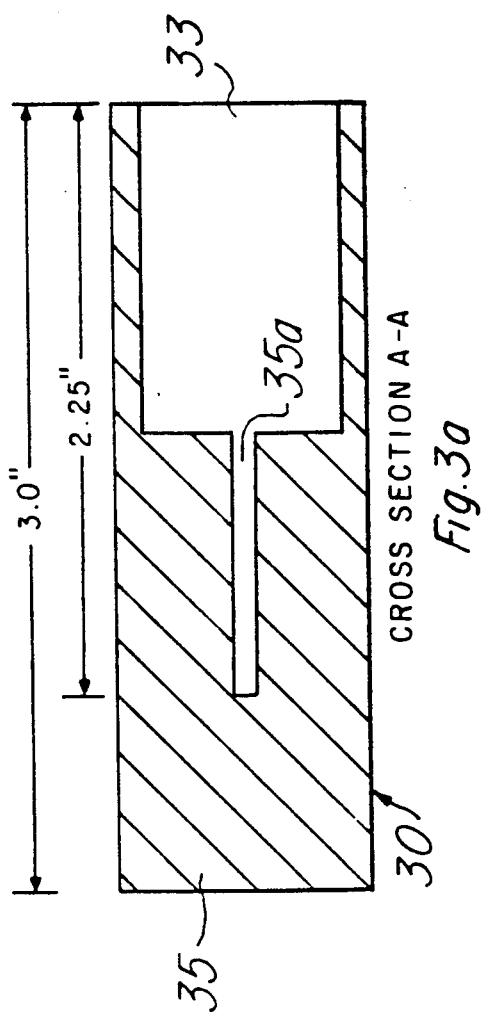
FIG. 3a is a cross-sectional view of the light diffuser of FIG. 3, taken along lines A—A.

In the preferred embodiment, the light diffuser 30 may have a solid end 35, as shown in FIG. 3a. End 35 may also have a hole 35a, into which the lead of a component may be inserted to assist in steadying the component being inspected.

The light diffuser 30 may also have a plug 37 as shown in FIG. 3c to guide an axial component into the light diffuser 30. The plug 37 fits into one end of viewing chamber 33 of light diffuser 30.

The fiber optic ring light 32 surrounds the light diffuser 30 and provides uniform lighting around the circumference of light diffuser 30. As indicated by dashed lines 32a of FIG. 2, the ring light 32 is focused onto the end of the light diffuser 30 containing the light chamber 33.

The combination of the ring light 32 and light diffuser 30 produces even illumination 360 degrees around the object being inspected. While the drawings show axial electronic components, the lighting system disclosed could be used to inspect any object which has problems with glare.

While it is not shown, there is also provided a means for supporting the component in place within the light diffuser 30. In the preferred embodiment, the component would be loaded into the inspection system and positioned within light diffuser 30 automatically. Well-known robotic equipment would preferably be used.

In the preferred embodiment, imaging of the lead being inspected is performed with a video camera system 40. However, the diffused lighting system 28 described above could also be used with human operators examining leads with a 10× microscope.

The video camera system 40 utilizes a known camera 41 and lens 42 to scan the lead through viewing hole 34. As shown in FIG. 2, the image field is displayed on a video monitor 43. The image of the lead is shown as 44, with defects shown as 45.

The signals generated by the video camera system 40 are analyzed automatically for solder coverage, eliminating the problems caused by human inspection techniques. The line of sight of the camera lens is preferably not quite vertical with respect to the longitudinal axis of light diffuser 30, so as to eliminate a shadow caused by viewing hole 34.

The video system produces an image of the leads being inspected, which must then be analyzed and processed in order to determine solder coverage. It is necessary to identify defects with the vision system, which requires a very consistent image with a high degree of contrast to allow the points of interest to be identified and analyzed.

The component to be inspected is loaded into the inspection system 20. In the preferred embodiment, a lead 21 of the component being tested is inserted into hole 33 in the end of light diffuser 30. The components are preferably loaded with automatic robotic apparatus, which is well-known.

The first step in the defect analysis process is to position the camera 40 and form an image through viewing hole 34. In processing the image formed, the image of the lead is located, using well-known techniques in image processing. Once the image of the lead is located, further processing is limited to the area defined by the boundaries of the lead image. FIG. 4 is a sample of a portion of an image field with the lead image indicated with the reference numeral 44. While the sample image area shown in FIG. 4 is 18 pixels by 25 pixels with the lead image 44 being 5 pixels wide, an actual image 515×512 pixels, with the lead image possibly being 170 pixels or so wide.

The lead image 44 is then sampled along its width and an average grayscale value is calculated. The sampling is preferably done at a number of points along the lead image 44, with all pixels in a column across the lead image 44 being sampled. The average value is then compared to a preselected value to determine if the lead is pretinned. If the lead is pretinned, the image processing goes on. The preselected value is empirically determined and supplied to the imaging software.

The next step in the process is to create a histogram of the entire lead image 44. The histogram is then analyzed, and a determination is made as to whether or not a valley on the histogram meets certain preselected criteria. The image processing software determines if the valley meets a certain profile, based upon preselected frequency and upper and lower grayscale values. This analysis determines the "background" coloration of the pretinned portion of lead image 44.

An advantage of the present invention is that the software can adjust for differing positions of the valley on the histogram, and thus adjust for differences in coloration of the pre-tinned areas of different components being inspected.

The histogram analysis also results in a "threshold" determination for the following process steps.

The lead image 44 is then examined pixel by pixel, and all pixels having a grayscale value below the "threshold" value based on histogram analysis set out above are changed to white. This allows an operator to visually inspect the lead image 44, if desired, and enables an operator to "see" the defects on the lead.

To determine the area of the lead image 44 covered by defects, the pixels having grayscale values below the threshold are added, and the total divided by the total pixels within lead image 44, with the result multiplied by 100, to get percent defect area. In the sample shown in FIG. 4, there are a total of 10 dark "defect" pixels 45 out of a total of 140 pixels, for a defect area which is 7% of the total lead.

The analysis described above is carried out for each separate view of the component being inspected. Since the video system 40 can only "see" a portion of the component through viewing hole 34, the component will typically be rotated so views around its entire periphery can be obtained. In the case of an axial component being inspected for solder coverage, the lead will typically be rotated 6 times, with each rotation being 60 degrees, for complete analysis of the entire periphery of the lead.

In the case of components which are not cylindrical like axial component leads, the number of "views" will depend upon the shape and type of inspection being done.

For a cylindrical object, since the video system 40 images more than a 60 degree arc of the component at a time, a windowing type process is done, such that only the 60 degree area at the center of the image is processed. In the case of a component lead, a masking process allows the image generated to follow any curvature of the lead. While in the preferred embodiment, the imaging processing described above is carried out separately for each 60 degree portion of the component being inspected, the entire lead could also be "flat-mapped", with all views being analyzed simultaneously.

Although the present invention has been described in detail, it should be understood that various changes, substitutions, and alterations could be made herein without departing from the spirit and scope of the invention as defined by the appended claims.

We claim:

1. An inspection system, comprising:

A cylindrical light diffusing inspection chamber, having an opening in at least one end, said cylindrical chamber having an outer wall, said outer wall having an opening therethrough into the interior of the cylindrical chamber, the chamber being adapted to received within the interior of the cylindrical chamber through said opening in said at least one end an object to be inspected, the object being coaxial with the chamber;

a light source coaxial with and surrounding the cylindrical inspection chamber, the light source providing continuous equal light intensity around the periphery of the cylindrical inspection chamber; and an imaging system disposed adjacent the inspection chamber for viewing an object in the inspection chamber through the opening in the outer wall, and mapping the surface reflectivity intensity of the object.

2. The inspection system of claim 1, wherein the imaging system comprises:

a video system.

3. The inspection system of claim 1, further comprising:

an image analyzing system for performing a grayscale analysis of the surface reflectivity intensity of the object and producing a histogram of the surface.

4. A method of inspecting objects, comprising the steps of:

inserting axially an object into one end of a cylindrical diffusion chamber;

illuminating the object with diffused lighting such that all areas of the object receive substantially equal amounts of light;

forming an image of the light intensity reflected from the surface of the object; and performing a grayscale analysis of the reflected light intensity from the surface of the object to determine color variations of the light reflected from the surface of the object.

5. The method according to claim 4, including the step of rotating the object in steps to form an image of the light intensity reflected from the entire surface of the object.

6. An inspection system, for inspecting an object including a light source and an illumination chamber, comprising:

a light source;

a fiber optic ring light receiving light from the light source and centered on an axis;

a cylindrical viewing chamber having light diffusing walls, co-axial with and positioned within said ring light;

said cylindrical viewing chamber having an opening in one end thereof for receiving a uniformly illuminated object to be inspected within said chamber; and a longitudinal opening in the viewing chamber wall for viewing the object to be inspected with a vision system;

said longitudinal opening has sloping walls to minimize light reflection into the inspection chamber through the longitudinal opening.

7. The inspection chamber according to claim 6, wherein said opening in said viewing chamber is co-axial with the walls of the viewing chamber.

* * * * *